(12) United States Patent
Wang et al.

(10) Patent No.: US 10,894,363 B2
(45) Date of Patent: Jan. 19, 2021

(54) BIOPRINTER AND CALIBRATION METHOD OF THE BIOPRINTER

(71) Applicant: REVOTEK CO., LTD, Sichuan (CN)

(72) Inventors: Deming Wang, Chengdu (CN); Yijun Li, Chengdu (CN)

(73) Assignee: Revotek Co., Ltd, Sichuan (CN)

( * ) Notice: Subject to any disclaimer, the term of this patent is extended or adjusted under 35 U.S.C. 154(b) by 426 days.

(21) Appl. No.: 16/067,569

(22) PCT Filed: Dec. 30, 2015

(86) PCT No.: PCT/CN2015/099796
§ 371 (c)(1),
(2) Date: Jun. 29, 2018

(87) PCT Pub. No.: WO2017/113157
PCT Pub. Date: Jul. 6, 2017

(65) Prior Publication Data
US 2019/0001579 A1    Jan. 3, 2019

(51) Int. Cl.
*B29C 64/232* (2017.01)
*B29C 64/393* (2017.01)
(Continued)

(52) U.S. Cl.
CPC .............. *B29C 64/393* (2017.08); *A61F 2/02* (2013.01); *B29C 64/209* (2017.08);
(Continued)

(58) Field of Classification Search
CPC ................................... B29C 64/232
See application file for complete search history.

(56) References Cited

U.S. PATENT DOCUMENTS

| 6,628,322 B1 | 9/2003 | Cerruti et al. |
| 2008/0213419 A1* | 9/2008 | Skubic .................. B29C 64/118 425/113 |

(Continued)

FOREIGN PATENT DOCUMENTS

| CN | 104057612 | 9/2014 |
| CN | 104786505 A | 7/2015 |

(Continued)

OTHER PUBLICATIONS

International Search Report and Written Opinion for PCT/CN2015/099796, dated Oct. 18, 2018.

(Continued)

*Primary Examiner* — Timothy Kennedy
(74) *Attorney, Agent, or Firm* — Wolf, Greenfield & Sacks, P.C.

(57) ABSTRACT

The present invention relates to the bioprinting technical field, and in particular relates to a bioprinter and a calibration method thereof. The bioprinter provided by the present invention comprises a control device, a first detection device, and a second detection device, wherein the first detection device is capable of sending a first signal to the control device when the spray device moves to a first position along the Z-axis direction such that the control device calibrates the preset length value of the spray device, and the second detection device is capable of sending a second signal to the control device when the second detection device moves to a second position along the Z-axis direction such that the control device calibrates the preset height value of the printing material initial adhesion surface. The present invention can automatically calibrate the preset length value of the spray device and the preset height value of the printing material initial adhesion surface, which can not only simplify the operation and reduce the labor intensity of the operator, but also effectively improve the mea- (Continued)

surement accuracy, ensure consistent accuracy between multiple measurements, and improve the operational reliability.

16 Claims, 6 Drawing Sheets

(51) Int. Cl.
  *B33Y 30/00* (2015.01)
  *A61F 2/02* (2006.01)
  *B33Y 50/02* (2015.01)
  *B29C 64/209* (2017.01)
  *B29C 64/106* (2017.01)

(52) U.S. Cl.
  CPC ............ *B29C 64/232* (2017.08); *B33Y 30/00* (2014.12); *B33Y 50/02* (2014.12); *B29C 64/106* (2017.08)

(56) References Cited

U.S. PATENT DOCUMENTS

| | | |
|---|---|---|
| 2012/0200626 A1 | 8/2012 | Orr |
| 2014/0117575 A1 | 5/2014 | Kemperle et al. |
| 2015/0037445 A1 | 2/2015 | Murphy et al. |
| 2016/0068793 A1* | 3/2016 | Maggiore ............. B29C 64/227 435/289.1 |
| 2016/0121535 A1* | 5/2016 | Li ........................ B29C 64/236 425/131.1 |
| 2016/0129633 A1* | 5/2016 | Huang .................. B29C 64/232 264/40.7 |
| 2016/0354980 A1* | 12/2016 | Ho ........................ B29C 64/393 |

FOREIGN PATENT DOCUMENTS

| | | |
|---|---|---|
| CN | 104842559 | 8/2015 |
| CN | 105014958 | 11/2015 |
| CN | 105058787 A | 11/2015 |
| CN | 105167879 | 12/2015 |
| CN | 105662648 | 6/2016 |

OTHER PUBLICATIONS

International Preliminary Report on Patentability for PCT/CN2015/099796, dated Jul. 3, 2018.
Extended European Search Report and Search Opinion for EP 15911786.0, dated Jul. 26, 2019.
[No Author Listed], The Xack: Bed auto leveling (capacitive) + E3D Hotend (RepRapPro Mendel). YouTube. Jul. 27, 2014. Screenshot. Retrieved from the Internet: URL:https://www.youtube.com/watch?v=MjDHaB07zic.
EP 15911786.0, Jul. 26, 2019, Extended European Search Report and Search Opinion.

* cited by examiner

BIOPRINTER AND CALIBRATION METHOD OF THE BIOPRINTER

RELATED APPLICATIONS

This application is a national stage filing under 35 U.S.C. § 371 of International Patent Application Serial No. PCT/CN2015/099796, filed Dec. 30, 2015, the content of which is incorporated herein by reference in its entirety.

TECHNICAL FIELD

The present invention relates to the technical field of bioprinting, and in particular relates to a bioprinter and a calibration method of the bioprinter.

BACKGROUND ART 3D bioprinting is a technology of printing biological materials (including natural biological materials and synthetic biological materials or cellular solutions) into a designed three-dimensional structure through the principles and methods of 3D printing. Compared with the ordinary 3D printing technology, the characteristics of the 3D bioprinting technology lies in that the biological tissues or organs printed by it further present certain biological functions and need to provide conditions for further growth of the cells and tissues. Therefore, the 3D bioprinting technology is confronted with many specific technical problems different from the ordinary 3D printing technology during its development.

The bioprinter, namely the device implementing the 3D bioprinting printing technology, uses living cells as bio-ink, and the bio-ink is sprayed out by a moving spray head and finally arranged into a biological tissue with a predetermined structure. In order to continuously adjust the printing position of the spray head in the printing process and finally accomplish 3D printing according to a predetermined design solution and a preset path, the spray head is normally connected to a three-dimensional motion platform, and the bio-ink sprayed from the spray head is attached to a printing carrier as needed. The printing carrier here includes a printing platform, a rotary rod in a rotary printing device, or a carrier such as a culture dish attached to the printing platform.

At present, a length value of the spray head, a height value of the printing material initial adhesion surface on the printing carrier, and a height distance between the bottom end of the spray head at the initial position and the printing material initial adhesion surface are typically preset in the printing program of the bioprinter. During each printing, the spray head is firstly controlled to move to a proper printing position according to the preset height distance between the bottom end of the spray head and the printing material initial adhesion surface in the printing program, and then the printing is started according to a preset path. However, since the printing carrier to which the bio-ink is adhered may often change, i.e. the height of the printing material initial adhesion surface often varies, and spray heads of different lengths may also be often replaced during use, an error between the actual height distance between the bottom end of the spray head and the printing material initial adhesion surface and the preset height distance in the printing program exists. For such height distance error, the existing solution is to manually measure the actual height of the printing material initial adhesion surface as well as the actual height of the spray head, and manually input them into the printing program to adjust and correct the preset values of corresponding parameters in the printing program. This is not only cumbersome in operation, but also easily affected in accuracy by the operational level of personnel, so that mismeasurement and incorrect input easily occur, and there is a poor consistency in accuracy.

CONTENT OF THE INVENTION

One technical problem to be solved by the present invention is that: in the existing bioprinter, the height variation of the location to which the bio-ink is adhered and the length variation of the spray head can only be measured and input manually, which is not only cumbersome in operation, but also low in accuracy and poor in reliability.

In order to solve the aforementioned technical problem, the present invention provides a bioprinter, which comprises a Z-axis movement assembly moving along a Z-axis direction of the bioprinter, a spray device, a platform, a control device, a first detection device, and a second detection device, wherein the platform is provided with a printing material initial adhesion surface, and under the drive of the Z-axis movement assembly, the spray device moves close to or away from the first detection device and the second detection device moves close to or away from the printing material initial adhesion surface, during which the first detection device is configured to send a first signal to the control device when the spray device moves to a first position along the Z-axis direction such that the control device calibrates a preset length value of the spray device, and the second detection device is configured to send a second signal to the control device when the second detection device moves to a second position along the Z-axis direction such that the control device calibrates a preset height value of the printing material initial adhesion surface.

Optionally, the control device includes a signal receiving apparatus, a height acquisition apparatus, and a calibrating apparatus, wherein the signal receiving apparatus is used to receive the first signal sent by the first detection device and the second signal sent by the second detection device, the height acquisition apparatus is used to respectively acquire an actual height value of the corresponding Z-axis movement assembly after the signal receiving apparatus receives the second signal and receives the first signal, and the calibrating apparatus is used to calibrate the preset length value of the spray device and the preset height value of the printing material initial adhesion surface according to a difference between the actual height value and the preset height value of the Z-axis movement assembly.

Optionally, the Z-axis movement assembly is driven by a drive motor, and the height acquisition apparatus is used to acquire the actual height value of the Z-axis movement assembly by acquiring a rotation angle of the drive motor when the Z-axis movement assembly stops.

Optionally, at the first position, a bottom end of the spray device abuts against the first detection device.

Optionally, the spray device is a spray head; or, the spray device includes a spray head and an extension rod, wherein the extension rod is disposed below the outlet of the spray head with a distance, inside the extension rod an elongated flow passage is provided for guiding fluid printing units of the biological printing material to perform an oriented spray, and the bottom end of the spray device for abutting against the first detection device is namely a bottom end of the extension rod.

Optionally, the spray device comprises a spray head and an extension rod, wherein an open recess, whose outlet communicates with the flow channel, is provided on an end surface of the extension rod adjacent to the spray head, the spray head extends into the open recess, the open recess is tapered toward the flow channel, an auxiliary material flow channel is formed between an outer wall of the spray head and the open recess, and a cavity is formed between the outlet of the spray head and the outlet of the open recess, thus the auxiliary material fluid passing through the auxiliary material flow channel wraps a main material fluid sprayed from the outlet of the spray head in the chamber, and fluid printing units are formed then.

Optionally, the flow channel is tapered from its inlet to outlet.

Optionally, the cross-section of the flow channel taken along a flow direction of the fluid printing unit is tapered.

Optionally, the first detection device includes a laser meter.

Optionally, at the second position, a bottom end of the second detection device abuts against the printing material initial adhesion surface.

Optionally, the bioprinter further comprises a telescoping control device, wherein the telescoping control device is connected with the Z-axis movement assembly as well as the second detection device, and the telescoping control device is configured to control the bottom end of the second detection device to move a certain distance toward the printing material initial adhesion surface.

Optionally, the telescoping control device is configured to control the bottom end of the second detection device to move vertically a distance toward the printing material initial attachment surface.

Optionally, the telescoping control device includes a cylinder, wherein the cylinder barrel of the cylinder is connected with the Z-axis movement assembly, and the cylinder rod of the cylinder is connected with the second detection device.

Optionally, the telescoping control device further includes a linear retaining device, and the linear retaining device is configured to maintain the straightness of the second detection device.

Optionally, the linear retaining device includes a chute and a clamping block in sliding connection with the chute, wherein the chute is connected to the cylinder barrel of the cylinder, the clamping block is connected to the second detection device, and the clamping block and the second detection device are moveable together along the chute.

Optionally, the second detection device includes an inductive measuring head.

A second aspect of the present invention also provides a calibration method for the bioprinter according to the first aspect of the present invention. The method comprises the following steps:

the Z-axis movement assembly drives the spray device of the bioprinter to the first position, and the first detection device sends the first signal to the control device;

after receiving the first signal, the control device calibrates the preset length value of the spray device;

the Z-axis movement assembly drives the second detection device of the bioprinter to the second position, and the second detection device sends the second signal to the control device;

after receiving the second signal, the control device calibrates the height preset value of the printing material initial adhesion surface.

Optionally, after receiving the first signal, the method further comprises the following steps:

the control device controls the Z-axis movement assembly to stop moving and acquires an actual height value of the Z-axis movement assembly;

the control device acquires a length variation of the spray device by calculating the variation between the actual height value and the preset height value of the Z-axis movement assembly;

and the control device calibrates the preset length value of the spray device according to the length variation of the spray device.

Optionally, after receiving the second signal, the method further comprises the following steps:

the control device controls the Z-axis movement assembly to stop moving and acquires an actual height value of the Z-axis movement assembly;

the control device acquires a height variation of the printing material initial adhesion surface by calculating the difference between the actual height value and the preset height value of the Z-axis movement assembly;

the control device calibrates the preset height value of the printing material initial adhesion surface according to the height variation of the printing material initial adhesion surface.

In the present invention, by providing a control device, a first detection device and a second detection device, the bioprinter is configured to automatically calibrate the preset length value of the spray device and the preset height value of the printing material initial adhesion surface. As there is no need to depend on manual measurement and input by labor in this case, it not only can simplify the operation and reduce the labor intensity of the operator, but also can effectively improve the measurement accuracy, ensure consistent accuracy between multiple measurements, and improve the operational reliability.

Other features of the present invention and advantages thereof will become explicit by means of the following detailed descriptions of exemplary embodiments of the present invention with reference to the drawings.

BRIEF DESCRIPTION OF THE DRAWINGS

In order to more clearly explain the embodiments of the present invention or the technical solutions in the prior art, a brief introduction will be given below for the drawings required to be used in the description of the embodiments or the prior art. It is obvious that, the drawings illustrated as follows are merely some of the embodiments of the present invention. For a person skilled in the art, he or she may also acquire other drawings according to these drawings on the premise that no inventive effort is involved.

IN THE DRAWINGS

1. Z-axis movement assembly; 2. Spray head assembly; 21. Spray head; 22. Extension rod; 221. Flow channel; 222.

Open recess; 223. Thermal insulation member; 23. Mounting block; 31. Cylinder; 32. Chute 33. Clamping block; 34. Inductive measuring head; 4. Culture dish; 5. Platform; 6. Laser Surveying Instrument; 7. Base; 8. Mounting plate.

EMBODIMENTS

Thereinafter, the technical solution in the embodiments of the present invention will be explicitly and completely described in combination with the drawings in the embodiments of the present invention. Apparently, the described embodiments are merely part of the embodiments of the present invention, rather than all the embodiments. The following descriptions of at least one exemplary embodiment which are in fact merely descriptive, by no device serve as any delimitation on the present invention as well as its application or use. On the basis of the embodiments of the present invention, all the other embodiments acquired by a person skilled in the art on the premise that no inventive effort is involved fall into the protection scope of the present invention.

The techniques, methods, and apparatuses known to a common technical person in the relevant art may not be discussed in detail, but in appropriate cases, these techniques, methods, and apparatuses should be considered as part of the granted description.

In the description of the present invention, it is necessary to understand that, the azimuth or positional relations indicated by such azimuth terms as "front, rear, up, down, left, right", "transverse, vertical, perpendicular, horizontal" and "top, bottom", are usually based on the azimuth or positional relations illustrated by the drawings, and are only for facilitating description of the present invention and simplifying the description. Unless otherwise specified, such azimuth terms do not indicate or imply that the device or element has to present a particular azimuth or to be constructed and operated in a particular azimuth, so that these azimuth terms cannot be considered as limitation on the protection scope of the present invention. The azimuth terms "inside" and "outside" mean the interior and exterior relative to the contour of various members themselves.

In the description of the present invention, it is necessary to understand that, words such as "first" and "second" which are used to define the parts, are only intended to distinguish the corresponding parts. Unless otherwise specified, the aforementioned words do not have particular meanings, and thus cannot be understood as limitation on the protection scope of the present invention.

FIGS. 1-4 show a schematic view of the structure of the bioprinter according to a first embodiment of the present invention. With reference to FIGS. 1-4, the bioprinter provided by the present invention comprises a Z-axis movement assembly 1 moving along a Z-axis direction of the bioprinter, a spray device, a platform 5, a control device, a first detection device, and a second detection device.

The platform 5 is provided with a printing material initial adhesion surface, and under the drive of the Z-axis movement assembly 1, the spray device moves close to or away from the first detection device and the second detection device moves close to or away from the printing material initial adhesion surface, wherein the first detection device is configured to send a first signal to the control device when the spray device moves along a Z-axis direction to a first position, such that the control device calibrates a preset length value of the spray device, and the second detection device is configured to send a second signal to the control device when the second detection device moves along the Z-axis direction to a second position, such that the control device calibrates a preset height value of the printing material initial adhesion surface.

By being provided with a control device, a first detection device and a second detection device, the bioprinter of the present invention is configured to automatically calibrate the preset length value of the spray device and the preset height value of the printing material initial adhesion surface. As there is no need to depend on manual measurement and input by labor in this case, it not only can simplify the operation and reduce the labor intensity of the operator, but also can effectively improve the measurement accuracy, ensure consistent accuracy between multiple measurements, and improve the operational reliability.

Further, the present invention also provides a calibration method for the bioprinter of the present invention, which comprises the following steps:

the Z-axis movement assembly 1 drives the spray device of the bioprinter to the first position by, and the first detection device sends the first signal to the control device;

after receiving the first signal, the control device calibrates the preset length value of the spray device;

the Z-axis movement assembly 1 drives the second detection device of the bioprinter to the second position, and the second detection device sends the second signal to the control device; and after receiving the second signal, the control device calibrates the preset height value of the printing material initial adhesion surface.

As one embodiment of the bioprinter in the present invention, the first detection device is configured to control the control device to start to measure the length variation of the spray device when a bottom end of the spray device moves along the Z-axis direction to the first position, wherein the first signal is a signal for controlling the control device to start to measure the length variation of the spray device, and the control device starts to measure the length variation of the spray device after receiving the first signal and calibrates the preset length value of the spray device in accordance with the length variation of the spray device; and/or, the second detection device is configured to control the control device to start to measure the height variation of the printing material initial adhesion surface, wherein the second signal is a signal for controlling the control device to start to measure the height variation of the printing material initial adhesion surface, and the control device starts to measure the height variation of the printing material initial adhesion surface after receiving the second signal and calibrates the preset height value of the printing material initial adhesion surface according to the height variation of the printing material initial adhesion surface.

Based on the embodiment, signals sent to the control device by the first and/or second detection device make the control device start measuring the variation and then compensate the variation to the corresponding preset value, thus the preset value is calibrated. The variation here refers to the length variation of the spray device corresponding to the first detection device or the height variation of the printing material initial adhesion surface corresponding to the second detection device.

In the embodiment, since the spray device and the second detection device both move along the Z-axis under the drive of the Z-axis movement assembly 1, the control device can effectuate the variation measurement by measuring the height variation of the Z-axis movement assembly 1. For example, the control device may effectuate calibrating the preset length value of the spray device in the following steps: after receiving the first signal, the control device stops the Z-axis movement assembly 1 and acquires an actual height value of the Z-axis movement assembly 1; then, the control device acquires the length variation of the spray device by calculating a difference between the actual height value and the preset height value of the Z-axis movement assembly 1; afterwards, the control device calibrates the preset length value of the spray device according to the length variation of the spray device. Similarly, the calibration of the preset height value of the printing material initial adhesion surface by the control device may also be implemented in the following steps: after receiving the second signal, the control device stops the Z-axis movement assembly 1 and acquires an actual height value of the Z-axis movement assembly 1; then, the control device acquires the height variation of the printing material initial adhesion surface by calculating a difference between the actual height value and the preset height value of the Z-axis movement assembly 1; afterwards, the control device calibrates the preset height value of the printing material initial adhesion surface according to the height variation of the printing material initial adhesion surface.

Figure 6:
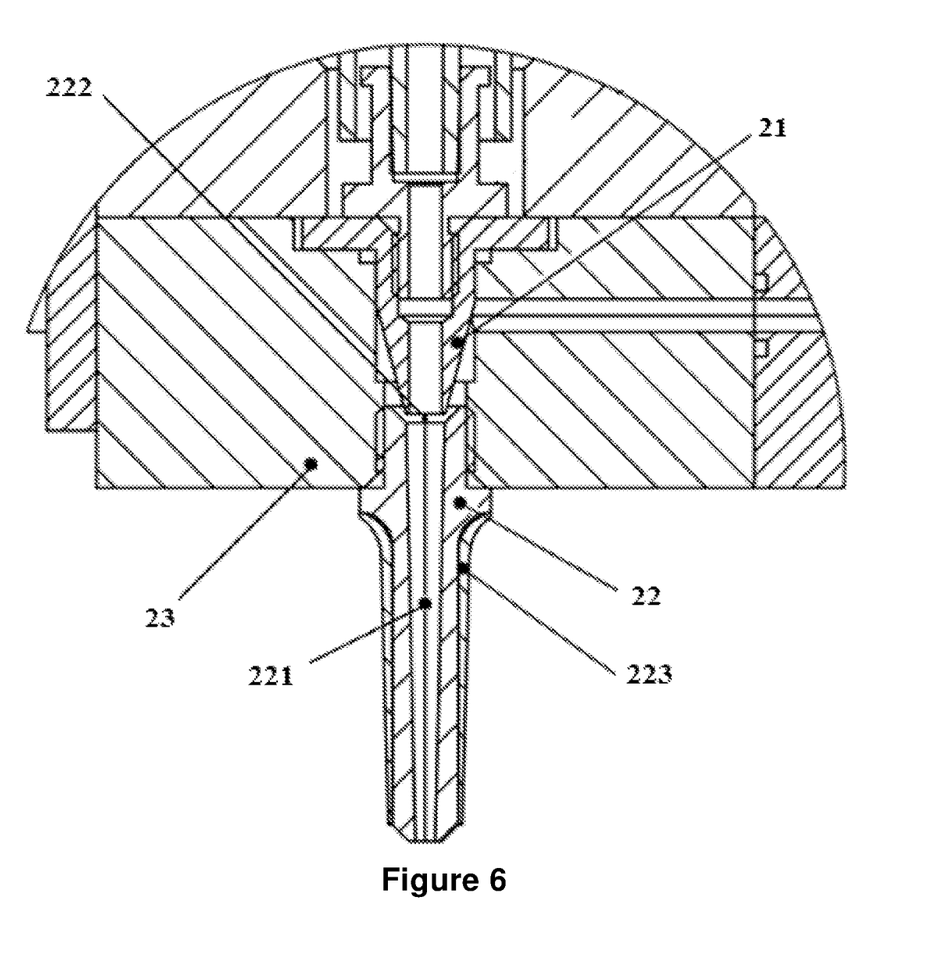
FIG. 6 shows a schematic view of a structure of the spray device of the bioprinter according to a second embodiment of the present invention.

As shown in FIG. 1-FIG. 4, the spray device of the present invention may include only the spray head 21, which means the printing material is directly sprayed from the outlet of the spray head 21 to the printing material adhesion surface. In this case, the bottom end of the spray device abutting against the first detection device is a bottom end of the spray head 21. However, as shown in FIG. 6, the spray device of the present invention may also include not only the spray head 21, but further include an extension rod 22, wherein the extension rod 22 is disposed below the outlet of the spray head 21 with a distance, and inside the extension rod 22 an elongated flow channel 221 is provided for guiding fluid printing units of the biological printing material to perform an oriented spray. In this case, the bottom end of the spray device abutting against the first detection device is a bottom end of the extension rod 22.

In the following, the aforementioned embodiments will be further explained respectively for the two cases in which the spray device includes only the spray head 21 and the spray device includes the spray head 21 and the extension stem 22.

A first embodiment in which the spray device includes only the spray head 21 will first be described in combination with FIG. 1-4. As illustrated in FIG. 1-4, the bioprinter of the embodiment includes a Z-axis movement assembly 1, a mounting plate 8, a spray head assembly 2, a platform 5, a base 7, a control device (not shown), a first detection device, a second detection device and a telescoping control device, wherein the spray head assembly 2 includes a spray device which is namely a spray head 21 in this embodiment.

The platform 5 is disposed on the base 7, and a culture dish 4, whose bottom wall is located on by printing material initial adhesion surface, is placed on the platform 5. The spray head assembly 2 is connected to the mounting plate 8 and the mounting plate 8 is connected with the Z-axis movement assembly 1, thus the spray head 21 is able to move longitudinally together with the mounting plate 8 along the Z-axis direction under the drive of the Z-axis movement assembly 1. As can be seen, in the embodiment, the platform 5 and the culture dish 4 remain stationary in the Z-axis direction, while the spray head 21 is configured to move close to or away from the platform 5 and the culture dish 4 along the Z-axis direction.

Figure 2:
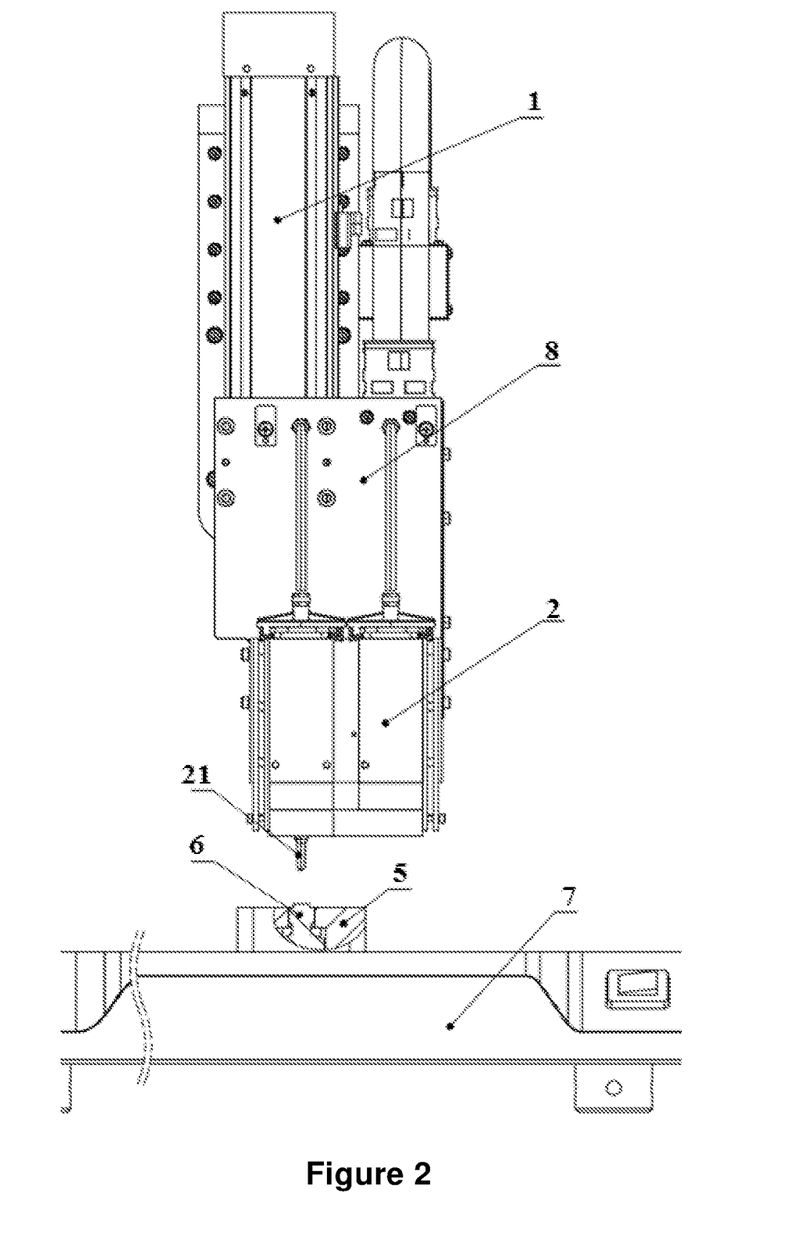
FIG. 2 shows a left view of FIG. 1.
Figure 3:
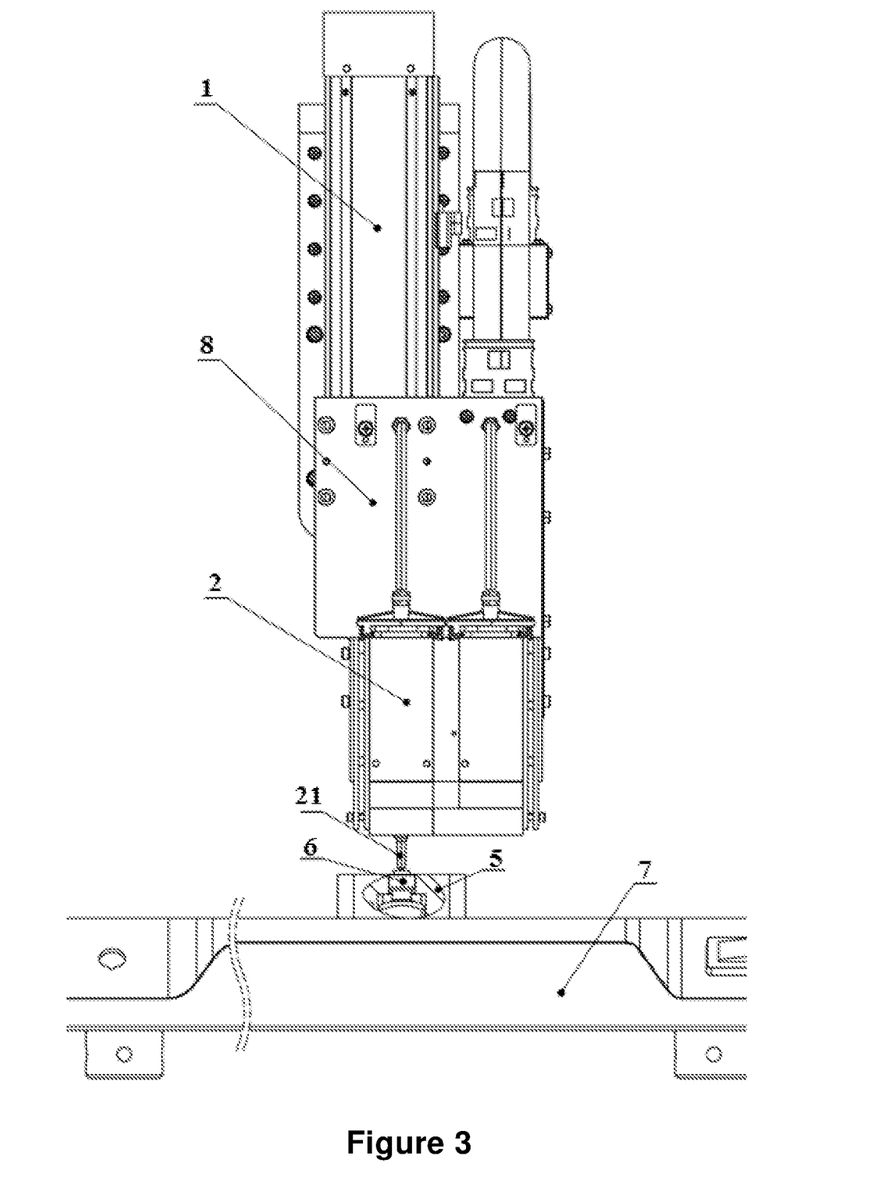
FIG. 3 shows a schematic view of an operation state of the first detection device according to the embodiment shown in FIG. 1.

As shown in FIG. 2 and FIG. 3, in the embodiment, the first detection device includes a laser surveying instrument 6 disposed on the platform 5, and the laser surveying instrument 6 is configured to send the control device a first signal which enables the control device start to measure the length variation of the spray head 21 when the spray head 21 moves to the first position. Moreover, in the embodiment, the laser surveying instrument 6 is also a pressure-sensitive detection device, i.e., it needs to be pressed before sending the first signal. Therefore, as illustrated in FIG. 3, at the first position, the laser surveying instrument 6 abuts against the bottom end of the spray head 21. In this way, when the spray head 21 approaches and presses the laser surveying instrument 6 under the drive of the Z-axis movement assembly 1, the laser surveying instrument 6 will send out the first signal to the control device, and when it is not necessary to measure the length of the spray head 21, the spray head 21 can be driven to move away from the laser surveying instrument 6 by the Z-axis movement assembly 1. In the embodiment, the laser surveying instrument 6 is with a measurement accuracy of 1 micron.

Figure 1:
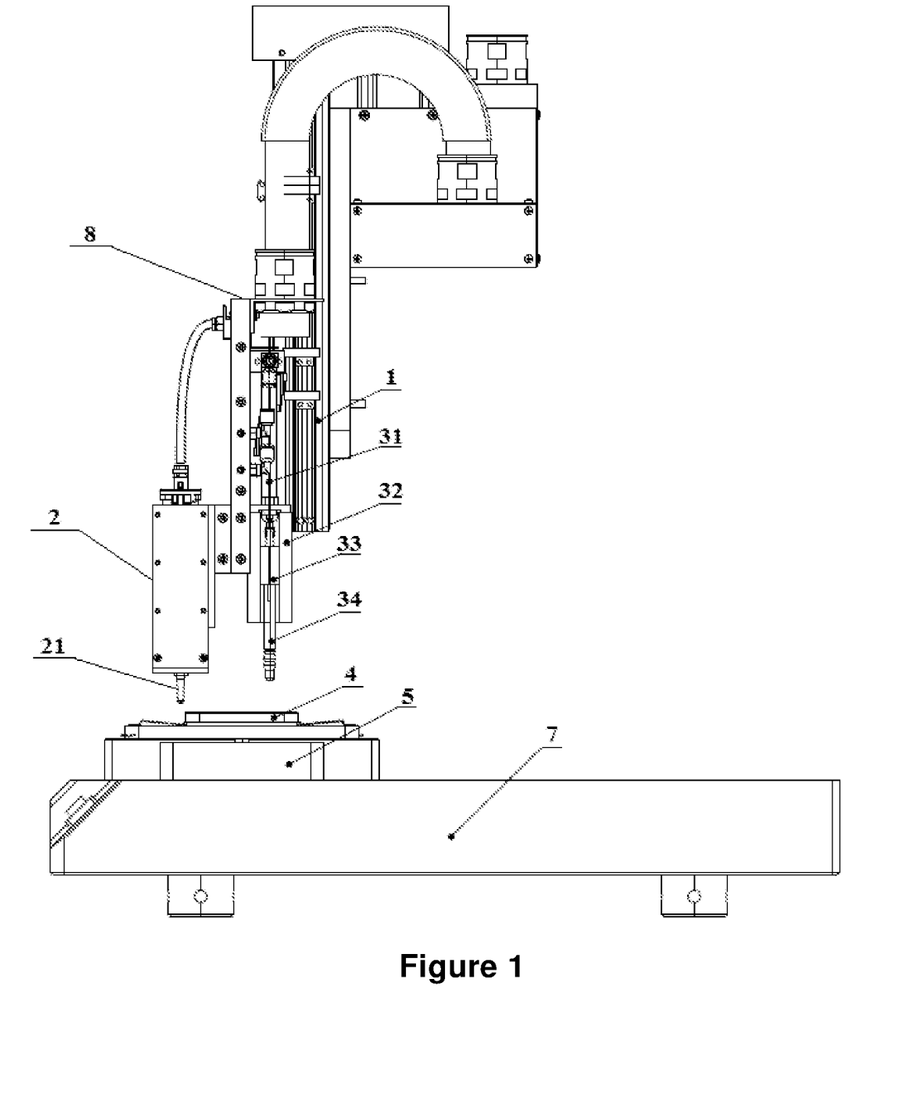
FIG. 1 shows a front view of the bioprinter according to the first embodiment of the present invention.
Figure 4:
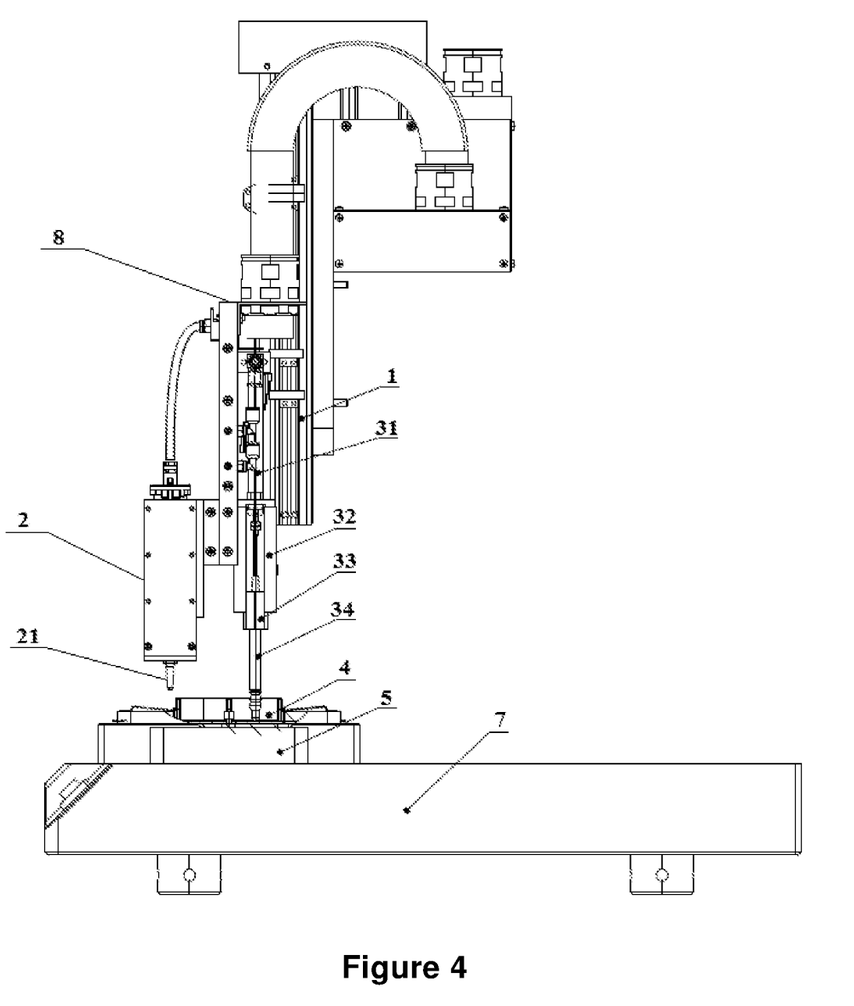
FIG. 4 shows a schematic view of an operation state of the second detection device according to the embodiment shown in FIG. 1.

As shown in FIG. 1 and FIG. 4, in the embodiment, the second detection device includes an inductive measuring head 34, and the inductive measuring head 34 is configured to send the control device a second signal which makes the control device start to measure the height variation of the bottom wall of the culture dish 4 when the inductive measuring head 34 moves to the second position along the Z-axis direction. Moreover, in the embodiment, the inductive measuring head 34 is a pressure-sensitive detection device, i.e., it needs to be pressed before sending the second signal. Therefore, as illustrated in FIG. 4, at the second position, the bottom end of the inductive measuring head 34 abuts against the printing material initial adhesion surface. In the embodiment, the inductive measuring head 34 is with a measurement accuracy of 1 micron.

In the embodiment, the telescoping control device is for controlling the bottom end of the inductive measuring head 34 to move a certain distance towards the bottom wall of the culture dish 4. As shown in FIG. 1 and FIG. 4, the telescoping control device comprises a cylinder 31, and the cylinder barrel of the cylinder 31 is connected to the Z-axis movement assembly 1 through the mounting plate 8, while the cylinder rod of the cylinder 31 is connected to the inductive measuring head 34. In this way, when the mounting plate 8 moves longitudinally along the Z-axis direction under the drive of the Z-axis movement assembly 1, the cylinder 31 and the inductive measuring head 34 can move longitudinally along the Z-axis together with the Z-axis movement assembly 1, thus away from or close to the bottom wall of the culture dish 4, namely close to or away from the printing material initial adhesion surface.

By providing the cylinder 31, when it is necessary to calibrate the preset height value of the printing material initial adhesion surface, the cylinder 31 is inflated to make the inductive measuring head 34 further moves a certain distance towards the bottom wall of the culture dish 4 along with a projecting action of the cylinder rod of the cylinder 31; and when it is unnecessary to perform calibration, the inductive measuring head 34 is driven away from the bottom wall of the culture dish 4 with the cylinder rod of the cylinder 31 being controlled to retract, so that the inductive measuring head 34 is prevented from producing unnecessary effects on normal operation of other components.

In addition, the cylinder 31 is of a high control accuracy. Under the action of the cylinder 31, the inductive measuring head 34 can be pushed out vertically, so that the inductive measuring head 34 can be perpendicular to the bottom wall of the culture dish 4 when coming into contact with the bottom wall of the culture dish 4. This can avoid delay in sending out the second signal which further results in inaccurate measurement results due to the inclination of the inductive measuring head 34. Moreover, since the cylinder 31 controls the telescoping of the cylinder rod with gas which is clean and may not cause pollution to the bioprinter, the influence of oil pollution on the biological properties of the printing material can be avoided.

In the embodiment, in order to further keep the inductive measuring head 34 perpendicular to the bottom wall of the culture dish 4 after the inductive measuring head 34 being pressed by the bottom wall of the culture dish 4, the telescoping control device further includes a linear retaining device. As illustrated in FIG. 1 and FIG. 2, the linear retaining device comprises a chute 32 and a clamping block 33 in slidable connection with the chute 32, wherein the chute 32 is connected to the cylinder barrel of the cylinder 31, the clamping block 33 is connected to the inductive measuring head 34, and the clamping block 33 as well as the inductive measuring head 34 can move together along the chute 32. By providing the chute 32 and the clamping block 33, the inductive measuring head 34 not only has a better straightness when being pushed out by the cylinder 31, but also can still maintain vertical abutment against the bottom wall of the culture dish 4 in the process of being pressed by the bottom wall of the culture dish 4, thus more accurate measurement results being acquired.

In the embodiment, the control device includes a signal receiving apparatus, a height acquisition apparatus, and a calibrating apparatus, wherein the signal receiving apparatus is used to receive the second signal sent by the inductive measuring head 34 and the first signal sent by the laser surveying instrument 6, the height acquisition apparatus is used to acquire the actual height value of the corresponding Z-axis movement assembly 1 after the signal receiving apparatus receives the second signal and the first signal, and the calibrating apparatus is used to calibrate the preset height value of the printing material initial adhesion surface and the preset length value of the spray head 21 according to the variation value between the actual height value and the preset value of the Z-axis movement assembly 1.

The height acquisition apparatus may acquire the actual height value of the Z-axis movement assembly 1 in a plurality of manners. Among them, since in the existing bioprinter, the Z-axis movement assembly 1 is driven by the drive motor, and a rotation angle of the drive motor can reflect a motional displacement of the Z-axis movement assembly 1, the height acquisition apparatus may acquire the actual height value of the Z-axis movement assembly 1 by acquiring the rotation angle of the drive motor when the Z-axis movement assembly 1 stops moving, such that the object of the present invention may be realized on the premise of making minor changes to the structure of the existing bioprinter.

As a more preferred embodiment, the Z-axis movement assembly 1 is driven by a servo motor whose encoder value reflects the rotation angle value, and the height acquisition apparatus acquires the actual height value of the Z-axis movement assembly 1 by acquiring the encoder value of the servo motor when the Z-axis movement assembly 1 stops moving.

The operational principles of the control device in the embodiment are as follows:

When the signal receiving apparatus of the control device receives the first signal, the control device controls the Z-axis movement assembly 1 to stop moving, and the height acquisition apparatus starts to acquire the current height value of the Z-axis movement assembly 1 (i.e., the actual height value of the Z-axis movement assembly 1) and transfer it to the calibrating apparatus, then the calibrating apparatus calculates the height variation of the Z-axis movement assembly 1 based on the actual height value of the Z-axis movement assembly 1 acquired by the height acquisition apparatus and the preset height value of the Z-axis movement assembly 1. Since it's after the laser surveying instrument 6 is pressed that the first signal is sent to the signal receiving apparatus by the spray head 21 every time, the length variation of the spray head 21 is equal to the height variation of the Z-axis movement assembly 1. Thus, the height variation of the Z-axis movement assembly 1 calculated by the calibrating apparatus at this time is actually the length variation of the spray head 21. Therefore, when the height variation of the Z-axis movement assembly 1 is compensated to the original preset length value of the spray head 21 by the calibrating apparatus, the calibrated preset length value of the spray head 21 can be acquired, and the calibration process of the preset length value of the spray head 21 is completed.

Similarly, when the signal receiving apparatus of the control device receives the second signal, the control device controls the Z-axis movement assembly 1 to stop moving, and the height acquisition apparatus starts to acquire the current height value of the Z-axis movement assembly 1 (i.e., the actual height value of the Z-axis movement assembly 1) and transfer it to the calibrating apparatus, then the calibrating apparatus calculates the height variation of the Z-axis movement assembly 1 based on the actual height value of the Z-axis movement assembly 1 acquired by the height acquisition apparatus and the preset height value of the Z-axis movement assembly 1. Since it's after the bottom wall of the culture dish 4 is pressed that the second signal is sent to the signal receiving apparatus by the inductance probe 34 every time, the height variation of the bottom wall of the culture dish 4 is equal to the height variation of the Z-axis movement assembly 1. Thus, the height variation of the Z-axis movement assembly 1 obtained by the calibrating apparatus is actually the height variation of the bottom wall of the culture dish 4, which is also the height variation of the printing material initial adhesion surface. Therefore, by compensating the height variation of the Z-axis movement assembly 1 to the given preset height value of the printing material initial adhesion surface, the calibrating apparatus can acquire the calibrated preset height value of the printing material initial adhesion surface, and complete the calibration process of the preset height value of the printing material initial adhesion surface.

Since the preset length value of the spray head 21 and the calibrated preset height value of the printing material initial adhesion surface are obtained, the calibrated height distance between the bottom end of the spray head 21 and the printing material initial adhesion surface can be acquired. Thus, after the spray head 21 moves to the printing material initial adhesion surface according to the calibrated height distance, the spray head 21 can accurately reach the position suitable for starting the printing, which effectively avoids problems such as device damage caused by inaccurate height distance between the bottom end of the spray head 21 and the printing material initial adhesion surface. For example, when the preset height value between the bottom end of the spray head 21 and the printing material initial adhesion surface is smaller than the actual value, the spray head 21 cannot reach the position suitable for printing after moving according to the corresponding height distance; while when the preset height value between the bottom end of the spray head 21 and the printing material initial adhesion surface is bigger than the actual value, even if having actually moved to the position suitable for printing, the spray head 21 won't stop, but will continue to move downwards until reach the position of the preset value, where the spray head 21 and the printing material initial adhesion surface abut with each other, thereby the spray head 21 and/or the printing material initial adhesion surface being damaged because of too much pressure.

Figure 5:
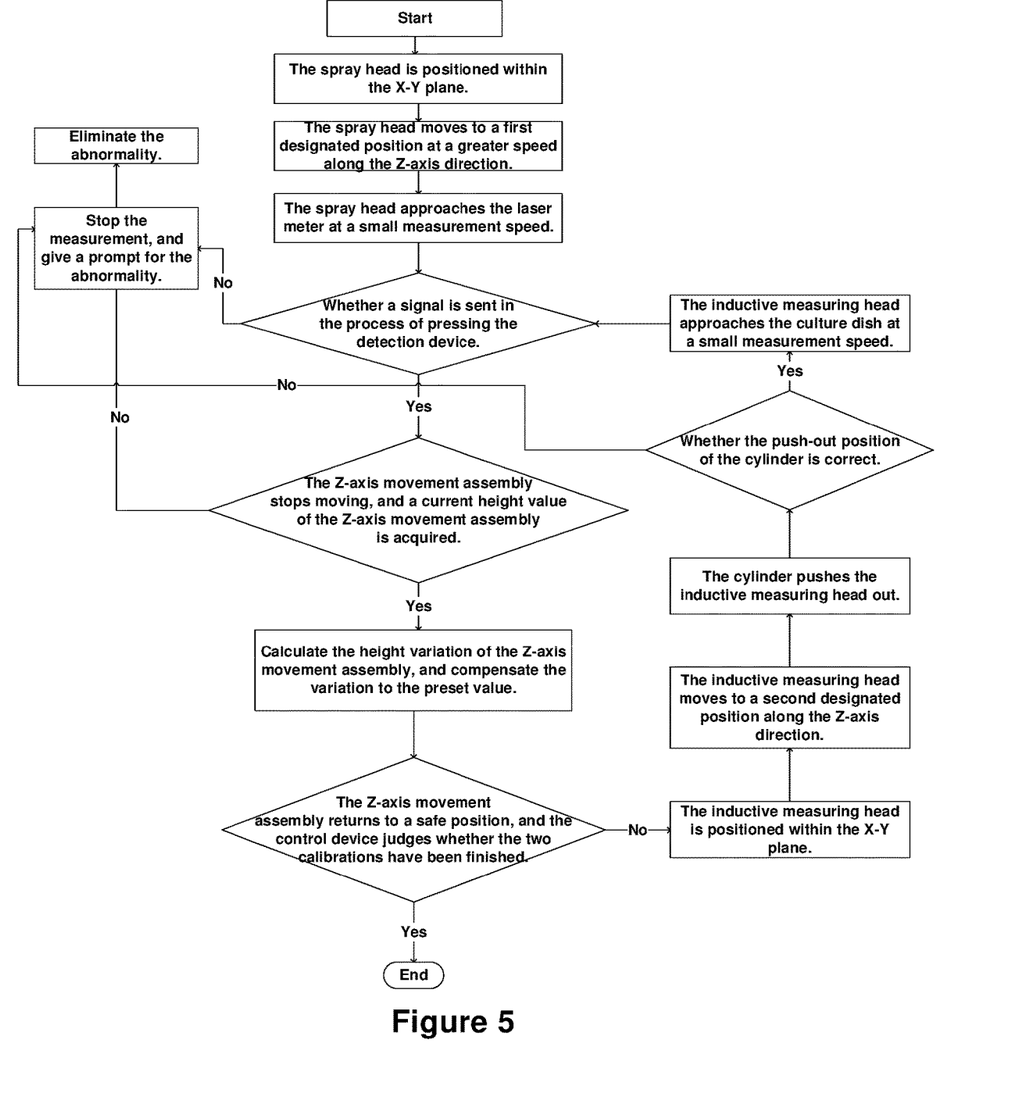
FIG. 5 shows a calibration flow chart of the bioprinter according to the embodiment shown in FIG. 1.

The process of calibrating the preset value by the bioprinter of the embodiment will be explained below in combination with the flow chart shown in FIG. 5.

(1) The spray head 21 is positioned in the X and Y directions. The spray head 21 is positioned within the X-Y plane so that the spray head 21 is aligned with the laser surveying instrument 6 within the X-Y plane.

(2) The spray head 21 is positioned in the Z direction. The Z-axis movement assembly 1 first rapidly moves at a greater speed to a first designated position, and then the Z-axis movement assembly 1 decelerates to a set measurement speed so that the spray head 21 slowly approaches the laser surveying instrument 6 at the measurement speed. Here, the first designated position is usually set at a position where a safety distance can be maintained between the spray head 21 and the laser surveying instrument 6. For example, it may be 10 mm below a reference set position.

(3) The length variation of the spray head 21 is measured. When the spray head 21 abuts against the laser surveying instrument 6 (namely the spray head 21 moves to the first position), the laser surveying instrument 6 sends the first signal to the control device, which makes the control device stop the Z-axis movement assembly 1 moving downwards further, record the current actual height value of the Z-axis movement assembly 1, and acquire the height variation of the Z-axis movement assembly 1, namely the length variation of the spray head 21, by calculating the difference between the actual height value of the Z-axis movement assembly 1 and the preset height value of the Z-axis movement assembly 1.

(4) The preset length value of the spray head 21 is calibrated. The control device compensates the length variation of the spray head 21 to the preset length value of the spray head 21, and completes the calibration of the preset length value of the spray head 21.

(5) After the calibration of the preset length value of the spray head 21 is completed, the control device controls the Z-axis movement assembly 1 to return to a safe position (i.e. the first designated position here), and judges whether the calibration of the preset height value of the printing material initial adhesion surface has been completed. If it is not completed, the following steps (6)-(10) are continued with. If it is completed, the calibration process is ended and the Z-axis movement assembly 1 returns to the reference set position.

(6) The inductive measuring head 34 is positioned in the X and Y directions. The inductive measuring head 34 is positioned within the X-Y plane so that the inductive measuring head 34 is aligned with the bottom wall of the culture dish 4 within the X-Y plane.

(7) The inductive measuring head 34 is positioned in the Z direction. First, the Z-axis movement assembly 1 rapidly moves to a second designated position at a greater speed. Then, the cylinder 31 is inflated so that the inductive measuring head 34 is pushed out. In the push-out process, the straightness of the push-out action is maintained together by the chute 32 and the clamping block 33. Afterwards, when the cylinder 31 is in place, for example after the lever of the cylinder 31 is fully extended, the Z-axis movement assembly 1 starts to slowly move towards the bottom wall of the culture dish 4 at a set measurement speed. Furthermore, the Z-axis movement assembly 1 is decelerated to a set measurement speed, such that the inductive measuring head 34 slowly approaches the bottom wall of the culture dish 4 at the measurement speed. Here, the second designated position is usually set at a position where a safety distance between the inductive measuring head 34 and the bottom wall of the culture dish 4 can be maintained. For example, it may be 30 mm below a reference set position.

(8) The height variation of the printing material initial adhesion surface is measured. When the inductive measuring head 34 abuts against the bottom wall of the culture dish 4 (namely the inductive measuring head 34 moves to the second position), the inductive measuring head 34 sends the second signal to the control device, which makes the control device stop the Z-axis movement assembly 1 further moving downwards, record the current actual height value of the Z-axis movement assembly 1, and acquire the height variation of the Z-axis movement assembly 1, i.e., the height variation of the printing material initial adhesion surface, by calculating the difference between the actual height value of the Z-axis movement assembly 1 and the preset height value of the Z-axis movement assembly 1.

(9) The preset height value of the printing material initial adhesion surface is calibrated. The control device compensates the height variation of the printing material initial adhesion surface to the original preset height value of the printing material initial adhesion surface, and completes the calibration of the preset height value of the printing material initial adhesion surface.

(10) After the calibration of the preset height value of the printing material initial adhesion surface is completed, the cylinder 31 is deflated, and the cylinder rod of the cylinder 31 is retracted, so that the cylinder rod of the cylinder 31 returns to the initial position, and controls the Z-axis movement assembly 1 to return to the reference set position, then the entire calibration process is completed.

Preferably, an abnormality detection step may also be included in the measurement process. For example, if no second signal is sent from the inductive measuring head 34 contacting with the bottom wall of the culture dish 4 to the inductive measuring head 34 pressing the bottom wall of the culture dish 4 a certain distance (for example 1 mm), or if no first signal is sent from the spray head 21 contacting with the laser surveying instrument 6 to the spray head 21 pressing the laser surveying instrument 6 a certain distance (for example 1 mm), or if the push-out position of the cylinder 31 is incorrect, the corresponding detection device or cylinder 31 is considered to be abnormal. After an abnormality occurs, the measurement can be ended, and a prompt for the abnormality can be given. The detection is resumed after the abnormality being eliminated.

It can be seen that, the bioprinter of the embodiment is configured to automatically measure the length variation of the spray head 21 and the height variation of the bottom wall of the culture dish 4 (i.e., the height of the printing material initial adhesion surface), and is able to complete automatic calibration of the corresponding preset value according to the automatically measured variation. Even if the length of the spray head 21 and/or the height of the bottom wall of the culture dish 4 are/is different during each printing, there is no need to perform artificial calibration on the preset length value of the spray head 21 and/or the preset height value of the bottom wall of the culture dish 4, which ensures that the spray head 21 can accurately move to a position suitable for printing during the printing process, thus effectively simplifying the operation process, lessening the labor intensity of the operator, improving the measurement precision and avoiding artificial errors. Moreover, on the basis of the automatic measurement and calibration process, when different specifications of spray heads 21 and culture dishes 4 are replaced, there is no need to change the control program of the control device, thereby improving the versatility of the control device.

Next, a second embodiment in which the spray device including the spray head 21 and the extension rod 22 will be explained in combination with FIG. 6. As shown in FIG. 6, the calibration process and the calibration principle of the second embodiment for the preset length value of the spray device and the preset height value of the printing material initial adhesion surface are basically the same as the first embodiment, and thus they are no longer repeated here. The differences between the second embodiment and the first embodiment lie in that, the spray device includes the spray head 21 and the extension rod 22, wherein the extension rod 22 is disposed below the outlet of the spray head 21 and disposed at a distance spaced from the outlet of the spray head 21. The extension rod 22 is internally provided with an elongated flow channel 221 for guiding fluid printing units of the biological printing material to perform an oriented spray. In the second embodiment, the bottom end of the spray device for abutting against the first detection device is the bottom end of the extension rod 22.

The fluid printing unit refers to the printing unit of a biological printing material, which may be a unit composed of a single main material fluid (bio-ink), and may also be a unit of mixed fluids consisting of a main material fluid wrapped with an auxiliary material fluid (hydrogel).

In the first embodiment, the spray device includes only the spray head 21, thus the printing material is directly sprayed to the printing material initial adhesion surface from the outlet of the spray head 21. As the outlet of the spray head 21 is suddenly narrowed, the fluid as printing material may be subject to damage caused by a mechanical force in the printing process. While the second embodiment additionally provides the extension rod 22 with the elongated flow channel 221 near the outlet of the spray head 21, such that the fluid printing unit as printing material is orientedly sprayed to the printing material initial adhesion surface through the flow channel 221. As the flow channel 221 is of an elongated shape, the fluid printing unit is subjected to a more uniform pressure in the process of being drained and sprayed by the flow channel 221, and the flow channel 221 is able to perform an oriented sequence on the fluid printing unit, thus a favorable flowability is easy to maintain, the possibility of occlusion is reduced, and the flow direction of the biological printing material becomes more stable, so that the crowding and compression between the cells is relieved, and the damage caused by the friction between the biological printing material and the metal material in the printing process is reduced. Further, for the fluid printing unit which is a mixed fluid printing unit formed by wrapping the main material fluid with the auxiliary material fluid, the flow channel 221 is also favorable for make the auxiliary material fluid uniformly wrap and protect the main material fluid. It can be seen that, the extension rod 22 with the elongated flow channel 221, is able to protect the printing material, reduce the damage on the printing material caused by the mechanical force in the printing process, and improve the reliability.

Furthermore, as shown in FIG. 6, the flow channel 221 is tapered from its inlet to outlet. The flow channel 221 is designed such that the fluid printing unit travels in the flow channel 221 to facilitate raising the flow rate of the fluid printing unit at the outlet of the flow channel 221 and reduce the possibility of its clogging. Preferably, the cross section of the flow channel 221 taken along the flow direction of the fluid printing unit is tapered. The tapered flow channel 221 in a structural form similar to a funnel or a subway gate makes a more uniform distribution of the fluid printing unit in the flow channel 221, and further reduces the possibility of its clogging. Moreover, the tapered flow channel which is easy to process, presents a favorable implementability.

Specifically or preferably, on the one hand, the inlet of the flow channel 221 is sized to be n times the size of the fluid printing unit, wherein n=2-5. Within the preferable size range, the problem of clogging at the inlet of the flow channel 221 can be effectively avoided. Preferably, the inlet of the flow channel 221 is sized to be twice the size of the fluid printing unit so that the inlet of the flow channel 221 is only accessible for two fluid printing units side by side at most. Since the flow channel 221 is a tapered flow channel, it is only possible to flow out a single row of fluid printing units reaching the outlet of the flow channel 221, such as to enable further reducing the possibility of the clogging of the fluid printing unit, and facilitating the spray of the fluid printing units in a single row.

On the other hand, the outlet of the flow channel 221 is sized to be 1-1.5 times, preferably 1.2 times the size of the fluid printing unit. Within the size range, the flow channel 221 not only facilitates the spray of the fluid printing units in a single row, but also can avoid that the auxiliary material fluid wraps the main material fluid in an excessive thickness in the case of ensuring that the main material fluid is not damaged, and facilitate further raising the flow rate of the fluid printing unit at the outlet of the flow channel, and ensure the continuity and uniformity of the spray of the fluid printing unit in a single row.

The flow channel 221 may be straight as shown in the drawings so that the fluid printing unit is sprayed downwards, and may also be arranged in a curved structural form according to the printing requirements, so as to provide more options in the spray direction.

Further, as shown in FIG. 6, an open recess 222 is provided on an end surface of the extension rod 22 adjacent to the spray head 21. An outlet of the open recess 222 communicates with the flow channel 221, and the spray head 21 extends into the open recess 222. The open recess 222 is tapered toward the flow channel 221, and an auxiliary material flow channel is formed between an outer wall of the spray head 21 and the open recess 222, and a cavity is formed between the outlet of the spray head 21 and the outlet of the open recess 222. The auxiliary material fluid passing through the auxiliary material flow channel wraps a main material fluid sprayed from the outlet of the spray head 21 in the chamber, so as to form a fluid printing unit.

By providing a tapered open recess 222 on an end face of the extension rod 22 adjacent to the spray head 21, an auxiliary material flow channel is formed between an outer wall of the spray head 21 and the open recess 222, and a cavity is formed between the outlet of the spray head 21 and the outlet of the open recess 222. The auxiliary material fluid (hydrogel) enters the chamber through the auxiliary flow channel and wraps the main material fluid (bio-ink) sprayed from the spray head, so as to form a mixed fluid printing unit. Among them, the main material fluid may be a homogeneous, non-homogeneous (e.g., granular mixture), continuous or discontinuous fluid.

Specifically, since an auxiliary material flow channel is formed between the outer wall of the spray head 21 and the tapered open recess 222, the auxiliary material flow channel has the function of making pressure uniform. Even if the auxiliary material enters the auxiliary material flow channel from one side as shown in FIG. 6, the auxiliary material still presents a uniform pressure intensity in the auxiliary material flow channel, thereby ensuring that the biological material presents a uniform wrapping effect at one side adjacent to or far from the auxiliary material inlet. In the embodiment, the section of the open recess 222 taken along the flow direction of the fluid printing unit, is preferably tapered, and the open recess 222 with a tapered structure allows the auxiliary material fluid to flow along a tapered face of the open recess 222, which produces the effect of converging towards the outlet of the spray head 21, and facilitates the uniform wrapping of the main material fluid unit by the auxiliary material fluid unit. The open recess 222 of the structural form can also ensure a more stable flow direction within the chamber.

The mixed fluid printing unit flows within the open recess 222, and the open recess 222 facilitates the convergence of the fluid printing unit toward the flow channel 221 of the extension rod 22, so as to ensure that the flow direction of the mixed fluid printing unit within the chamber is more stable, and avoid its diffusion in the auxiliary material flow channel.

As shown in FIG. 6, there is a gap between the outlet of the spray head 21 and the open recess 222. Specifically or preferably, the gap between the outlet of the spray head 21 and the open recess 222 is smaller than the size of the fluid printing unit, which can prevent the fluid printing unit from reversely flowing toward the auxiliary material flow channel, and ensure that the fluid printing unit within the chamber flows stably to the flow channel 221.

Based on the extension rod 22 of the embodiment, the process of wrapping the main material fluid with the auxiliary material fluid is as follows:

The main material fluid after being sprayed from the spray head 21, enters the chamber between the outlet of the spray head 21 and the outlet of the open recess 222. The auxiliary material fluid enters the chamber through the auxiliary material flow channel formed between the outer wall of the spray head 21 and the open recess 222. The auxiliary material fluid in the chamber has certain pressure, and the auxiliary material fluid is compressed such as to be adhered to a portion of the main material fluid unit projecting from the spray head 21. Until the entire main material fluid unit is sprayed, the auxiliary material fluid completely wraps the main material fluid unit, to form a mixed fluid printing unit. At this time, a portion of the fluid printing unit has already entered the flow channel 221 of the extension rod 22. Finally, the main material fluid unit enters the flow channel 221 of the extension rod 22 under the continuous wrapping of the auxiliary material fluid, and the main material fluid unit surrounded by the auxiliary material fluid orientedly flows within the flow channel 221, and is uniformly wrapped, and sequentially sprayed.

In the flow process, the main material fluid is adequately and uniformly wrapped by the auxiliary material fluid, so that the auxiliary material is uniformly and adequately wrapped. The auxiliary material fluid which is wrapped around the main material to form a protective structure before the main material fluid is sprayed from the outlet of the flow channel 221, further reduces the influence of the printing process over the main material fluid.

In addition, as shown in FIG. 6, the extension rod 22 with the flow channel 221 may be disposed at a position adjacent to the outlet of the spray head 21 by the mounting block 23. Further, a thermal insulation member 223 may also be provided on the outer periphery of the extension rod 22. The thermal insulation member 223 can ensure that the fluid printing unit keeps a desired temperature in the flow channel 221 and maintains the activity of the fluid printing unit.

It is necessary to explain that, the embodiments of the present invention are explained by only exemplifying a contact type inductive measuring head 34 and a laser surveying instrument 6. However, in fact, the second detection device and the first detection device may also choose a structural form in which a triggering signal for the control device can be sent out without being pressed. Moreover, in the embodiment, the printing material initial adhesion surface is located on the bottom wall of the culture dish 4, however, as a matter of fact, the printing material initial adhesion surface may also be located on the top surface of the platform 5 and on other printing carriers such as a rotary rod in the rotary printing device. These are all within the protection scope of the present invention.

The foregoing is intended only as an exemplary of the present invention, but is not used for limiting the present invention. Any amendment, equivalent replacement, improvement, and the like within the spirit and principles of the present invention should all be contained within the protection scope of the present invention.

The invention claimed is:

1. A bioprinter, comprising:

a Z-axis movement assembly, movable along a Z-axis direction of the bioprinter;

a platform, provided with a printing material initial adhesion surface;

a first detection device;

a second detection device, for moving close to or away from the printing material initial adhesion surface under the drive of the Z-axis movement assembly;

a spray device, for moving close to or away from the first detection device under a drive of the Z-axis movement assembly; and a control device;

wherein the first detection device is configured to send a first signal to the control device when the spray device moves to a first position along the Z-axis direction, such that the control device calibrates a preset length value of the spray device; and the second detection device is configured to send a second signal to the control device when the second detection device moves to a second position along the Z-axis direction, such that the control device calibrates a preset height value of the printing material initial adhesion surface.

2. The bioprinter according to claim 1, wherein the control device comprises:

a signal receiving apparatus, configured to receive the first signal sent by the first detection device and the second signal sent by the second detection device;

a height acquisition apparatus, configured to respectively acquire an actual height value of the corresponding Z-axis movement assembly after the signal receiving apparatus receives the second signal and receives the first signal; and a calibrating apparatus, configured to calibrate the preset length value of the spray device and the preset height value of the printing material initial adhesion surface according to a difference between the actual height value and the preset height value of the Z-axis movement assembly.

3. The bioprinter according to claim 2, wherein the Z-axis movement assembly is configured to be driven by a drive motor, and the height acquisition apparatus is configured to acquire the actual height value of the Z-axis movement assembly by acquiring a rotation angle of the drive motor when the Z-axis movement assembly stops.

4. The bioprinter according to claim 2, wherein at the first position, a bottom end of the spray device abuts against the first detection device.

5. The bioprinter according to claim 4, wherein,
the spray device is a spray head; or
the spray device comprises a spray head and an extension rod, wherein the extension rod is disposed below the outlet of the spray head with a distance, inside the extension rod an elongated flow channel is provided for guiding fluid printing units of the biological printing material to perform an oriented spray, and the bottom end of the spray device for abutting against the first detection device is a bottom end of the extension rod.

6. The bioprinter according to claim 4, wherein the first detection device comprises a laser surveying instrument.

7. The bioprinter according to claim 2, wherein at the second position, a bottom end of the second detection device abuts against the printing material initial adhesion surface.

8. The bioprinter according to claim 7, further comprising a telescoping control device, wherein the telescoping control device is connected with the Z-axis movement assembly as well as the second detection device, and the telescoping control device is configured to control the bottom end of the second detection device to move a certain distance toward the printing material initial adhesion surface.

9. The bioprinter according to claim 8, wherein the telescoping control device is configured to control the bottom end of the second detection device to move vertically a distance toward the printing material initial attachment surface.

10. The bioprinter according to claim 9, wherein the telescoping control device comprises a cylinder, wherein the cylinder barrel of the cylinder is connected with the Z-axis movement assembly, and the cylinder rod of the cylinder is connected with the second detection device.

11. The bioprinter according to claim 10, wherein the telescoping control device further comprises a linear retaining device for maintaining the straightness of the second detection device.

12. The bioprinter according to claim 11, wherein the linear retaining device comprises a chute and a clamping block in sliding connection with the chute, wherein the chute is connected to the cylinder barrel of the cylinder, the clamping block is connected to the second detection device, and the clamping block and the second detection device are moveable together along the chute.

13. The bioprinter according to claim 7, wherein the second detection device comprises an inductive measuring head.

14. A calibration method for the bioprinter according to claim 1, comprising steps as follows:
the Z-axis movement assembly drives the spray device of the bioprinter to the first position, and the first detection device sends the first signal to the control device;
after receiving the first signal, the control device calibrates the preset length value of the spray device;
the Z-axis movement assembly drives the second detection device of the bioprinter to the second position, and the second detection device sends the second signal to the control device; and
after receiving the second signal, the control device calibrates the height preset value of the printing material initial adhesion surface.

15. The calibration method according to claim 14, wherein after receiving the first signal, the method further comprises steps as follows:
the control device stops the Z-axis movement assembly and acquires an actual height value of the Z-axis movement assembly;
the control device acquires a length variation of the spray device by calculating a difference between the actual height value and the preset height value of the Z-axis movement assembly; and
the control device calibrates the preset length value of the spray device according to the length variation of the spray device.

16. The calibration method according to claim 14, wherein after receiving the second signal, the method further comprises steps as follows:
the control device stops the Z-axis movement assembly and acquires an actual height value of the Z-axis movement assembly;
the control device acquires a height variation of the printing material initial adhesion surface by calculating the difference between the actual height value and the preset height value of the Z-axis movement assembly; and
the control device calibrates the preset height value of the printing material initial adhesion surface according to the height variation of the printing material initial adhesion surface.

* * * * *